(12) United States Patent
Bernardelli

(10) Patent No.: US 6,815,543 B1
(45) Date of Patent: Nov. 9, 2004

(54) PROCESS FOR CATALYZING THE OXIDATION OF ORGANIC COMPOUNDS

(75) Inventor: Patrick Bernardelli, Fontenay Aux Roses (FR)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/049,208

(22) PCT Filed: Aug. 9, 2000

(86) PCT No.: PCT/EP00/07726

§ 371 (c)(1), (2), (4) Date: Feb. 8, 2002

(87) PCT Pub. No.: WO01/10797

PCT Pub. Date: Feb. 15, 2001

Related U.S. Application Data

(60) Provisional application No. 60/150,101, filed on Aug. 20, 1999, and provisional application No. 60/148,079, filed on Aug. 10, 1999.

(51) Int. Cl.$^7$ ..................... C07D 487/22; A61K 31/555
(52) U.S. Cl. ........................................ 540/145; 540/504
(58) Field of Search ................................. 540/145, 504

(56) References Cited

FOREIGN PATENT DOCUMENTS

| DE | 4101334 A | 8/1991 |
|---|---|---|
| EP | 0342615 A | 11/1989 |
| WO | WO 96 08455 A | 3/1996 |

OTHER PUBLICATIONS (Battoni et al. Laboratoire de Chimie et Biochimie Pharmacoloques et Toxicologiques, Univ. Rene Descartes, Paris, Fr., Act. Dioxygen Homogeneous Catal. Oxid [Proc. Int. Symp], 5th (1993), 449.*
Yoon Jing Lee, Epoxidation of Olefins with H2O2 Catalyzed By An Electronegatively–substituted Iron Pdorphyrin Complex In Aprotic Solvent, Chemistry Letters, No. 8, pp. 837–838 (1998).
Still, et al., Rapid Chromatographic Technique for Preparative Separation with Moderate Resolution, J. Org. Chem, 43: 2923 (1978).
Felix, et al., Quinazolines and 1,4–Benzodiazepines. XLIII(1). Oxidations with Ruthenium Tetroxide, J. Heterocycl. Chem, 5: 731 (1968).
Sulkowski, et al., The Formation and Subsequent Rearrangment of 7–Chloro–5–phenyl–3,1, 4–benzoxadiazepin–2(1H)–one, J. Org. Chem., 27: 4424 (1962).
Battioni, et al., Monooxygenase–like Oxidation of Hydrocarbons by H2O2 Catalyzed by Manganese Porphyrins and Imidazole: Selection of the Best Catalytic System and Nature of the Active Oxygen Species, J. Am. Chem. Soc., 110: 8462 (1988).

Thellend, et al., Ammonium Acetate as a very Sime and Efficient Cocatalyst for Manganese Prophyrin–catalysed Oxgenation of Hydroarbons by Hydrogetn Peroxide, J. Chem. Soc., Chem. Comm., 1035 (1994).
Ebel, V.S., et al., Analytik und Synthese wichtiger 3–Hydroxy–5–phenyl–1,4–benzodiazepin–2–on–Derivate, Arzneim.–Forsch., 29:1317 (1979).
Rocha Gonsalves, et al., State of the art in the development of biomimetic oxidation catalysts, J. Mol. Catal. A: Chem., 113:209 (1996).
Frohlic, L. et al., Moglichkeiten des Einsatze biomimetischer System zur Monooxygenierung von Wirk–und Arzneistoffen, Pharm. Ind. 59:803 (1997).
Chorghade, M.S., et al., Metalloporphyrins as chemical mimics of cytochrome P–450 systems, Pure Appl. Chem. 68:753 (1996).
Meunier, B., Metalloporphyrins and Versatile Catalysts for Oxidation Reactions and Oxidative DNA Cleavage, Chem Rev., 92:1411 (1992).
Masumoto, H., Applications of Chemical Cytochrome P–450 Model Systems to Studies On Drug Metabolism, M. Drug Metab. Dispos, 19:768 (1991).
Seddon, T., et al., Comparative Drug Metabolism of Diazepam in Hepatocytes Isolated From Man, Rat, Monkey and Dog, Biochem. Phjarmacol., 38:1657 (1989).
Chenery, R.J., et al., Diazepam Metabolism in Cultured Hepatocytes from Rat, Rabbit, Dog, Guinea Pig, and Man, R. Drug Metab. Dispo., 15:312 (1987).
Andrews, S.M., et al., The metabolism and disposition of [2–14C]diazepam in the streptozotocin–diabetic rat, Xenobitica 14:751 (1984).
Schwandt, H.J., et al., Metabolic Rearrangements of 1,4–Benzodiazepine Derivatices, Xenobiotica 4:733 (1974).
Ruelius, H.W., et al., Metabolism of Diazepam in Dogs: Transformation to Oxazepam, Arch. Biochem. Biophys., III:376 (1965).
Schwartz, M.A., et al., Metabolism of Diazepam in Rat, Dog, and Man, J. Pharmacol. Exp. Ther., 149:423 (1965).
Ogawa, A., et al., Benzotrifluoride: A Useful Alternative Solvent for Organic Reactions Currently Conducted in Dichloromethane and Related Solvents, J. Org. Chem., 62:450 (1997).
Ono, S., et al., Human liver microsomal diazepam metabolism using cDNA–expressed cytochrome P450s: role of CYP2B6, 2C19 and the 3A subfamily, Xenobiotica, 26:1155 (1996).
Dolphin D., et al., Polyhaloporphyrins: Usual Ligands for Metals and Metal–Catalyzed Oxidations, Acc. Chem. Res., 30:251 (1997).

* cited by examiner

*Primary Examiner*—Mark L. Berch
*Assistant Examiner*—Kahsay Habte
(74) *Attorney, Agent, or Firm*—Claude F. Purchase, Jr.; Matthew Russo

(57) ABSTRACT

Oxidation of organic compounds is catalyzed by addition of a catalytic amount of a metalloporphyrin in a non-reactive aprotic solvent.

19 Claims, No Drawings

PROCESS FOR CATALYZING THE OXIDATION OF ORGANIC COMPOUNDS

This application claims the benefit of provisional applications No. 60/148,079 filed Aug. 10, 1999 and Ser. No. 60/150,101 filed Aug. 20, 1999.

FIELD OF THE INVENTION

The study of drug metabolism is an important part of the very expensive drug R&D process. In humans and other mammals, many drugs are metabolized through oxidative reactions catalyzed by heme- and cytochrome-containing enzymes. Cytochrome P450 mono-oxygenases, the main enzymes involved in drug oxidative metabolism, have in their active site a heme moiety.

Synthetic metalloporphyrins can serve favorably to mimic oxidative catalytic reactions occurring in biological systems, with the aim of producing and identifying oxidative products of drug candidates, in quantities allowing in vivo studies.

PCT application WO 90/08455 discloses a process for the preparation of oxidative products using various combinations of a synthetic metalloporphyrin, a co-oxidizing reagent, and a solvent. The solvent is generally a $CH_3CN/CH_2Cl_2$ combination. One of the major inconveniences of processes of this type is the fact that they frequently provide incomplete yields of the sought-after individual products as well as low conversion percentages. As a result, they can rarely be used in a reliable fashion in integrated discovery processes. In fact, their use is generally limited to experimental validation.

SUMMARY OF THE INVENTION

In accordance with the present invention, the inventor has unexpectedly found that the yields of oxidative reactions involving metalloporphyrins and which can be useful for the synthesis of metabolites of organic compounds of interest could be increased in a substantial manner through the use of an inert aprotic solvent.

Thus, one of the objects of the present invention is a process for the oxidation of organic compounds. This process comprises reacting the selected organic compound with catalytic amounts of a metalloporphyrin and of an oxidizing agent in the presence of an inert aprotic solvent and recovering the desired products obtained therefrom.

The process of the invention is extremely useful in pharmaceutical research and development as it can be used to perform preliminary evaluations of the metabolic processes which are likely to occur when a given compound is tested in vivo. These preliminary evaluations can be performed rapidly without having to carry out expensive and time consuming in vivo experiments. Furthermore, the process of the present invention provides better yields of individual products than those obtained using prior art processes. In other words, the process of the present invention opens the possibility of obtaining and analyzing in a more systematic fashion a higher number of individual potential metabolites for a given selected compound on which the process is carried out.

DETAILED DESCRIPTION OF THE INVENTION

The present invention therefore concerns a process for the efficient oxidative preparation of metabolites of organic compounds. The invention comprises reacting an organic compound of interest with a catalytic amount of a metalloporphyrin and an oxidizing agent, in a non-reactive aprotic solvent.

As mentioned previously, several drugs are metabolized through oxidative reactions. The process of the instant invention is therefore applied favorably to organic compounds of interest possessing one or several functional groups which will react to oxidation conditions. Some of these functional groups are described below but as the skilled person will readily appreciate, the list provided is not intended to be exhaustive. In fact, the process of the invention can be used on any organic compound which can be oxidized in some way by enzymes involved in drug oxidative metabolism.

Preferably, compounds containing heteroatoms, such as nitrogen or sulfur, can be efficiently oxidized through the process of the invention, particularly to a higher oxidation state, and more particularly to their highest oxidation state. For example, primary amines can be readily converted to their corresponding hydroxylamines, nitroso- or nitro-derivatives; and tertiary amines to their corresponding N-oxides.

Also, C—H bonds can be conveniently hydroxylated into C—OH bonds by metalloporphyrin-catalyzed oxidations according to this invention. Examples include labile C—H bonds, such as those in benzylic positions or C—H bonds wherein the carbon atom is adjacent to a heteroatom (e.g. N, S, O, or the like). Those are particularly reactive to these conditions.

In this manner, primary alcohols can be converted to their corresponding aldehydes; in turn aldehydes can be converted to their corresponding acids, and said acids may further undergo decarboxylation.

Through the process of the invention, secondary alcohols can be converted to their corresponding ketones.

Carbon-carbon double bonds can be epoxidized by metalloporphyrin-catalyzed oxidation according to this invention, and aromatic groups can be oxidized into corresponding phenols or quinones.

The main parameters involved in the process of the invention are the starting material which is usually an organic compound of interest, the reactants which usually include a metalloporphyrin, an oxidizing agent and an inert aprotic solvent, and the reaction conditions which comprise the reaction temperature and the reaction time. Each of these parameters will be discussed in further detail below.

Metalloporphyrins

Synthetic metalloporphyrins are described in international patent application WO 96/08455. The term "metalloporphyrin", as used herein, refers to porphyrin compounds of formula (I):

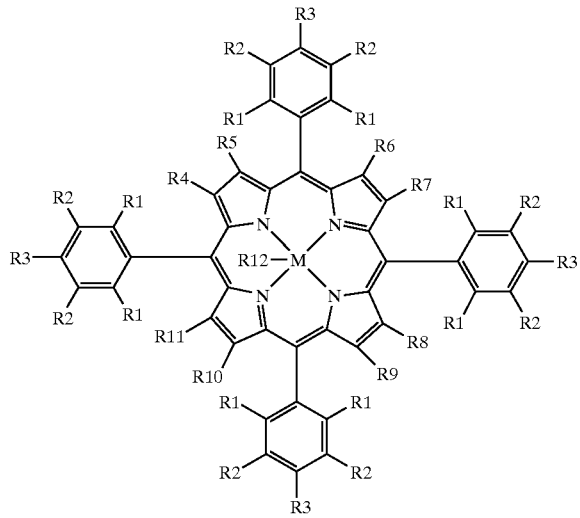

wherein:

R1, R2 and R3 independently represent hydrogen or an electron-withdrawing group such as Cl, F, Br, $SO_3Na$, or the like, R4, R5, R6, R7, R8, R9, R10 and R11 independently represent hydrogen or an electron-withdrawing group such as Cl, F, Br, $NO_2$, CN, $SO_3Na$ or the like, R12 is Cl, acetate or the like, M is selected from the group consisting of iron, manganese, chromium, ruthenium, cobalt, copper and nickel.

Preferred metalloporphyrins include tetrakis(pentafluoro-phenyl)porphyrin Mn(III) chloride, herein abbreviated as Mn(TPFPP)Cl, which is the compound of formula (I) above wherein M is manganese, R1, R2 and R3 are fluorine, R4, R5, R6, R7, R8, R9, R10 and R11 are hydrogen, and R12 is chlorine.

Preferred metalloporphyrins also include:

tetrakis(pentafluoro-phenyl)porphyrin Fe chloride, abbreviated as Fe(TPFPP)Cl, which is the compound of formula (I) above wherein M is iron, R1, R2 and R3 are fluorine, R4, R5, R6, R7, R8, R9, R10 and R11 are hydrogen, and R12 is chlorine;

tetrakis(2,6-dichlorophenyl)porphyrin Mn chloride, abbreviated as Mn(TDCPP)Cl, which is the compound of formula (I) above wherein M is manganese, R1 is chloride, R2, R3, R4, R5, R6, R7, R8, R9, R10 and R11 are hydrogen, and R12 is chlorine;

tetrakis(2,6-dichlorophenyl)porphyrin Fe chloride, abbreviated as Fe(TDCPP)Cl, which is the compound of formula (I) above wherein M is iron, R1 is chloride, R2, R3, R4, R5, R6, R7, R8, R9, R10 and R11 are hydrogen, and R12 is chlorine;

tetrakis(2,6-dichlorophenyl)-octachloroporphyrin chloride Fe, abbreviated as Fe(TDCPCl$_8$P)Cl, which is the compound of formula (I) above wherein M is iron, R1 is chloride, R2 and R3 are hydrogen, R4, R5, R6, R7, R8, R9, R10 and R11 are chloride, and R12 is chlorine;

the compound Mn((Cl$_2$Ph)$_4$(NO$_2$)P)Cl, of formula (I) above wherein M is manganese, R1 is chloride, R4 is NO2, R2, R3, R5, R6, R7, R8, R9, R10, and R11 are hydrogen, and R12 is chlorine;

the compound Mn((Cl$_2$Ph)$_4$(NO$_2$)$_2$P)Cl, of formula (I) above wherein M is manganese, R1 is chloride, R5 and R6 are NO$_2$, R2, R3, R4, R7, R8, R9, R10 and R11 are hydrogen, and R12 is chlorine.

The amount of the metalloporphyrin catalyst usually ranges between 0.5 and 10% molar and is preferably about 1% molar.

Oxidizing Agents

Various oxidizing agents can be used in the instant invention. It should be noted that the very nature of the oxidizing agent does not appear to be a limiting factor in the process of the present invention. The person skilled in the art can thus select the appropriate oxidizing agent among the wide variety of compounds which have been used in metalloporphyrin-catalyzed oxidative reactions. A list of possible agents includes, but is not limited to: iodosylbenzene, also known as iodosobenzene, aqueous solutions of hydrogen peroxide (concentration about 30 to 45%), anhydrous equivalents of hydrogen peroxide such as sodium percarbonate, urea hydrogen peroxide complex or the like, potassium monopersulfate, sodium hypochlorite, tert-butyl hydroperoxide, cumene hydroperoxide, m-chloroperbenzoic acid, and magnesium monoperoxyphthalate. Preferred oxidants include iodosylbenzene, any source of hydrogen peroxide, and potassium monopersulfate.

Oxidation using hydrogen peroxide is more efficient in the presence of a co-catalyst such as imidazole, ammonium acetate, N-hexylimidazole, amine N-oxides, tetrabutylammonium acetate, tert-butyl pyridine, pyridine, 4-methylpyridine, and 2,4,6-trimethyl-pyridine. For a review, see "State of the art in the development of biomimetic oxidation catalysts" Rocha Gonsalves, A. M.; Pereira, M. M. *J. Mol. Catal. A: Chem.* 1996, 113, 209.

Solvent

The metalloporphyrin-catalyzed oxidation of the invention is performed in an inert solvent, which in fact can contain one or several solvents. The term 'inert aprotic solvent', when used herein, is intended to designate any solvent or any mixture of solvents which, when evaluated in a global manner, does not react in any substantial fashion with the starting materials or with the products of the reaction. More particularly, the solvent should not react with the oxidizing agent. Furthermore, the solvent should be resistant to hydrogen abstraction.

In the case of a mixture of solvents, this mixture usually contains a so-called "main solvent" and a "co-solvent". It should be noted however that several solvents having similar properties could be used to form the main solvent. Similar considerations apply to an eventual mixture of co-solvents.

The main solvent is present in larger amounts in the solvent mixture than the co-solvent. In fact, it is the main solvent that confers its overall properties to the global solvent mixture, which will then play a key role in the process of the invention. The main solvent should therefore be inert and aprotic.

To the extent possible, the main solvent should have the capability to dissolve the starting material (i.e. the organic compound of interest) and the metalloporphyrin.

Examples of the main solvent include, but are not limited to polyhalogenated aliphatic solvents such as 1,1,2-trichloro-1,2,2-trifluoroethane and the like or polyhalogenated aromatic solvents such as 1,2-dichlorobenzene, 1,2,4-trichlorobenzene, pentafluorobenzene and the like. Preferred polyhalogenated solvents include polyfluorinated aromatic compounds, such as trifluorotoluene (also known as benzotrifluoride) and the like. Trifluorotoluene is a most preferred solvent, which combines the capacity of dissolving a wide variety of organic compounds with a low reactivity towards oxidative conditions. Although the skilled person can determine by routine experiments the optimal amount of main solvent to be used in each individual case, suitable concentrations of starting material in the chosen solvent can vary between 0.1 M and 0.5 M, preferably 0.1 M.

The co-solvent is present in small amounts in the mixture and is introduced to provide additional properties of interest to the overall solvent mixture, which will be useful at some point but which will not interfere in a significant manner with the reaction itself.

In a first embodiment of the process of the present invention, if any of the organic compound of interest or the oxidizing agent is not soluble in the main solvent, a co-solvent can be used to improve its solubility in the reaction medium.

For example, if the starting material is not soluble in trifluorotoluene or in any main solvent available, a co-solvent can be used in order to improve its solubility in the reaction medium. Preferred co-solvents include highly polar and poorly nucleophilic co-solvents. Preferably, the properties of the co-solvent should be chosen in order to minimize complex formation with the metalloporphyrin. 2,2,2-Trifluoroethanol and, particularly, 1,1,1,3,3,3-hexafluoropropan-2-ol (also called hexafluoroisopropanol or HFIP) are representative examples of co-solvents that can be used in the process of this invention. More particularly, hexafluoroisopropanol, can be useful in oxidation reactions performed with iodosylbenzene in one of the organic solvents mentioned above since this co-solvent helps dissolve this particular oxidant in the reaction medium.

The amount of co-solvent used to dissolve the starting material or the oxidizing agent and eventually the catalyst should be kept to relatively low levels with respect to the main solvent. Although the skilled person can determine by routine experiments the optimal amount of co-solvent to be used in each individual case, suitable concentrations can vary between 1 and 30%, preferably between 1 and 20% and more preferably between 1 and 10% with respect with the main solvent.

In a second embodiment of the process of the present invention, the co-solvent can be used in order to facilitate transfer of reactants within the reaction medium. For instance, a co-solvent is used in the case where the starting material or one or several reactants leads to a reaction mixture which comprises a biphasic solution.

For example, in the case where the oxidant is used as an aqueous solution, the reaction is biphasic and a water-miscible co-solvent can be used to facilitate the transfer of the oxidant in the organic phase. A minimal amount of co-solvent, such as hexafluoroisopropanol, is preferred. This co-solvent is miscible with water and it can facilitate dissolution of the starting material.

The amount of co-solvent which should be used in this second embodiment, as expressed in catalytic amounts, usually ranges between 0.25 and 1 equivalent, preferably between 0.3 and 0.5 and is more preferably about 0.4 equivalent with respect to the starting material.

As an alternative to this second embodiment of the invention, a phase-transfer catalyst can be used to facilitate the transfer of any of the reactants into the phase where the reaction will take place. For instance, when the oxidant is used as an aqueous solution, a phase-transfer catalyst can be used to facilitate the transfer of the oxidant in the organic phase.

Examples of phase-transfer catalysts include tetraalkyl ammonium salts (such as dodecyl-trimethyl-ammonium bromide and the like). The amount of phase-transfer catalyst which should be used in this second embodiment, as expressed in catalytic amounts, usually ranges between 0.05 and 0.5 equivalent and is more preferably about 0.10 equivalent with respect to the starting material.

Temperature and Duration of the Reaction

The reaction is carried out at a temperature between about −20° C. and 100° C., and preferably between about −10° C. and 40° C.

The skilled person should note however that sonication can be used to increase the reaction rate. The reaction is then preferably performed in an ultrasound bath cooled to 0° C.

Generally, the duration of the reaction varies from a few minutes up to 2 h. Advancement can be monitored with TLC or HPLC analytical techniques; thus the reaction is stopped when the oxidation reaction reaches a plateau point beyond which no substantial conversion is observed.

EXAMPLES

Without limiting the invention, the following examples illustrate the implementation of the processes of the invention.

The purity, identity and physico-chemical characteristics of the products prepared are determined as follows:

the purity is verified by analytical reverse-phase HPLC on a Merck Lachrom apparatus and the Rf observed is given for the eluent used;

the identity of the products obtained with the proposed structures is verified by their proton nuclear magnetic resonance spectrum and by mass spectrometry.

The $^1$H NMR spectra are recorded at 400 MHz on a Brüker instrument, the compounds being dissolved in deuterochloroform with tetramethylsilane as internal standard. The nature of the signals, their chemical shifts in ppm, the number of protons they represent and their exchange capacity with $D_2O$ are noted.

The mass spectra are recorded on a Micromass Platformn LC spectrometer (simple quadrupole with positive ionization electrospray). The infrared spectra are recorded on a Nicolet spectrometer.

The phrase "flash chromatography on a silica column" means a method adapted from that of Still et al. (1978) J. Org. Chem. 43: 2923. The purity of elution fractions is verified before they are gathered and evaporated.

The terms "evaporation", "elimination" or "concentration" of the solvents mean, possibly after desiccation on an appropriate dehydrating agent such as $Na_2SO_4$ or $MgSO_4$, a distillation under a pressure of 25 to 50 mm Hg (3,3 to 6,7 kPa) with moderate heating in a water bath at a temperature below 30° C.

Example 1

Oxidation of Diazepam (1) with Iodosylbenzene (PhIO) Catalyzed by tetrakis(pentafluorophenyl)porphyrin Manganese (III) Chloride in Trifluorotoluene During this reaction, nordiazepam (2), temazepam (3), oxazepam (4), 6-chloro-4-phenyl-1-methyl-2-(1H)-quinazolinone (5) and 6-chloro-4-phenyl-2-(1H)-quinazolinone (6) are formed.

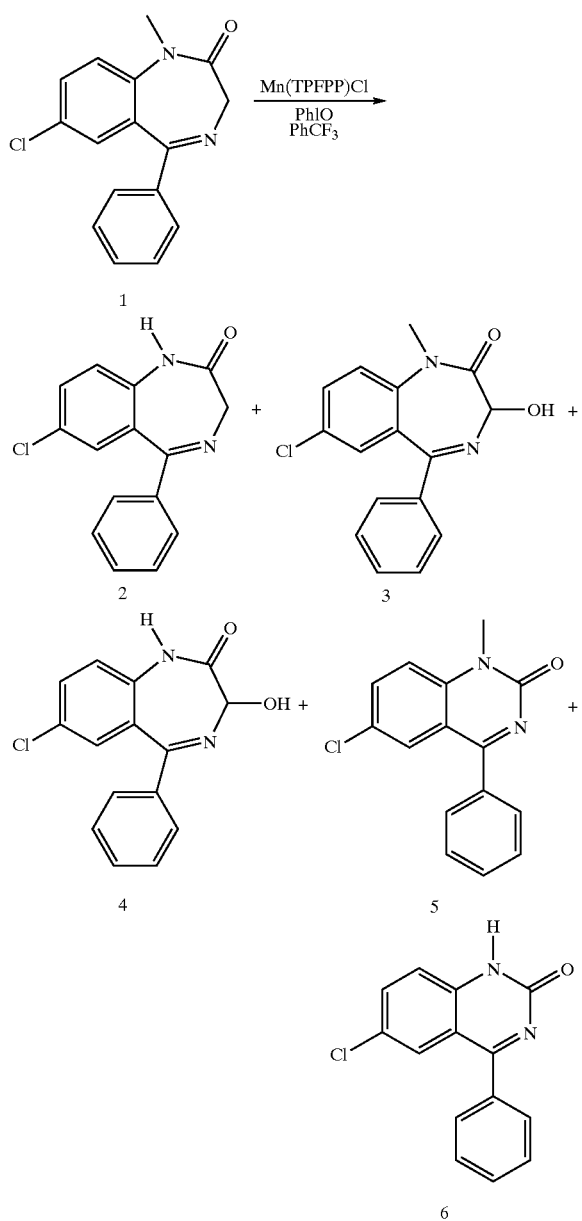

To 240 μL of a solution containing 25 μmol of diazepam (1) in trifluorotoluene is added 10 μL of a 25 mM solution of 5,10,15,20-tetrakis(pentafluorophenyl)-21H,23H-porphyrin manganese (III) chloride (0.25 μmol, 1 mol %) in trifluorotoluene. To the resulting stirring solution is added 3 times a portion of iodosylbenzene (3×5.5 mg, 3×25 μmol, 3 equiv.), one every hour. The reaction is monitored by analytical HPLC one hour after each addition: a sample, prepared with 5 μL of crude and 100 μL of a 5 mM methanolic solution of acetophenone (internal standard) diluted with 395 μL of methanol, is injected into a Nucleosil 5C18 150×4.6 mm column eluting with 50/50 methanol/water at 1 mL/min during 45 minutes. Nordiazepam (2), temazepam (3), oxazepam (4) formed are identified by comparison with authentic samples (Sigma). Their retention times are respectively 21.9, 16.7 and 13.3 min. Chloro-1-methyl-4-phenyl-1H-quinazolin-2-one (5) and 6-chloro-4-phenyl-1H-quinazolin-2-one (6), respectively eluting at 25.1 and 20.5 min, are identified in a separate run by isolation and comparison of $^1$H NMR and MS data with Felix et al (1968) J. Heterocycl. Chem. 5, 731 and Sulkowski et al (1962) J. Org. Chem. 27, 4424.

Yields of products from the reaction are shown in the following table:

| PhIO (equiv.) | Products obtained: Yield (%) | | | | | |
|---|---|---|---|---|---|---|
| | 1 | 2 | 3 | 4 | 5 | 6 |
| 1 | 31 | 19 | 12 | 3 | 4 | 0 |
| 2 | 5 | 17 | 6 | 7 | 11 | 4 |
| 3 | 1 | 9 | 2 | 5 | 10 | 3 |

Results form the reaction performed in 1:1 CH$_2$Cl$_2$/CH$_3$CN, solvent conditions representative of the state of the art, are shown below:

| PhIO (equiv.) | Products obtained: Yield (%) | | |
|---|---|---|---|
| | 1 | 2 | 3 |
| 1 | 86 | 1 | 1 |
| 2 | 83 | 1 | 2 |
| 3 | 79 | 1 | 2 |

Comparison of both sets of results implies that the use of a solvent such as trifluorotoluene instead of the classical dichloromethane/acetonitrile leads to better diazepam conversion, and formation of a higher number of products in significantly better yields.

Example 2

Oxidation of Diazepam (1) with a 30% Aqueous Solution of Hydrogen Peroxide Catalyzed by tetrakis (penatfluorophenyl)porphyrin manganese (III) Chloride in Trifluorotoluene This reaction is more efficient in the presence of catalytic amounts of imidazole (Battioni et al (1988) J. Am. Chem. Soc. 110, 8462) and ammonium acetate (Thellend et al (1994) J. Chem. Soc., Chem. Comm., 1035).

During this reaction, nordiazepam (2), temazepam (3), oxazepam (4), 6-chloro4-phenyl-1-methyl-2-(1H)-quinazolinone (5), diazepam N-oxide (2) and nordiazepam N-oxide (8) are formed.

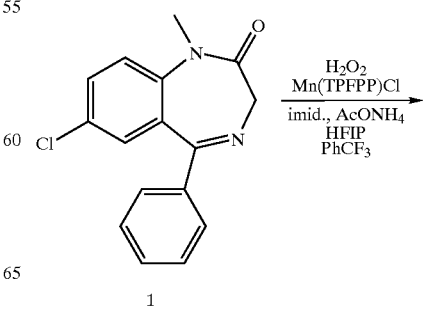

-continued

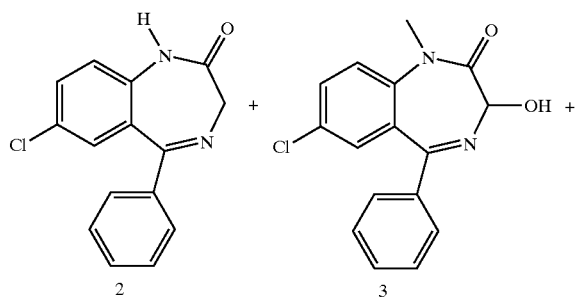

2       3

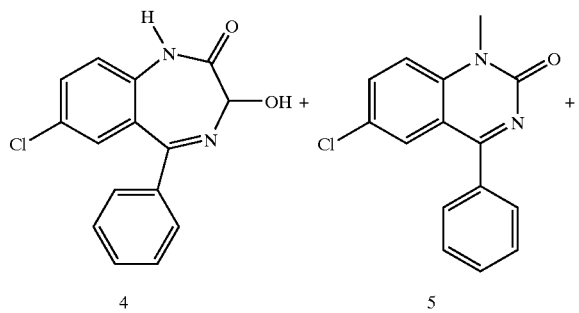

4       5

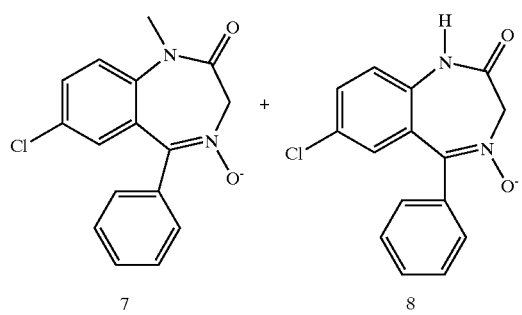

7       8

To 240 µL of a solution containing 25 µmol of diazepam (1) in trifluorotoluene is added 10 µL of a 25 mM solution of 5,10,15,20-tetrakis(pentafluorophenyl)-21H,23H-porphyrin manganese (III) chloride (0.25 µmol, 1 mol %) and 1,1,1,3,3,3-hexafluoro-2-propanol (1.1 µL, 10.4 µmol, 0.4 equiv.) in trifluorotoluene. To the resulting stirring solution is added dropwise an aqueous solution of 30% hydrogen peroxide (2.6 µL, 25 µmol, 1 equiv.), imidazole (6.5 µL of a 1 M aqueous solution, 6.5 µmol, 0.25 equiv.) and ammonium acetate (25 µL of a 1 M solution, 25 µmol, 1 equiv.) over two hours. Thirty minutes after the addition, the reaction is monitored by analytical HPLC in the same manner as in Example 1. One equivalent of 30% aqueous hydrogen peroxide (2.6 µL, 25 µmol, 1 equiv.) is then added every 10 minutes until 15 equivalents of oxidant are used. The reaction is monitored after the addition of 2, 5, 10 and 15 equiv. of hydrogen peroxide. Diazepam N-oxide (7) (retention time 8.4 min) and nordiazepam N-oxide (8) (6.7 min) are identified by comparison with samples prepared from the reaction of diazepam and nordiazepam with m-chloroperbenzoic acid (cf. Ebel et al (1979) Arzneim-Forsch. 29, 1317).

Yields of products from the reaction are shown in the following table:

| $H_2O_2$ (equiv.) | Products obtained: Yield (%) | | | | | | |
|---|---|---|---|---|---|---|---|
| | 1 | 2 | 3 | 4 | 5 | 7 | 8 |
| 1 | 71 | 4 | 7 | 0 | 1 | 5 | 0 |
| 2 | 58 | 8 | 10 | 1 | 1 | 9 | 1 |
| 5 | 41 | 10 | 13 | 1 | 3 | 10 | 1 |
| 10 | 26 | 10 | 12 | 2 | 5 | 8 | 2 |
| 15 | 19 | 10 | 14 | 2 | 8 | 6 | 2 |

Results form the analogous reaction performed in 1:1 $CH_2Cl_2/CH_3CN$, instead of trifluorotoluene and hexafluoroisopropanol as co-solvent, are shown below:

| $H_2O_2$ (equiv.) | Products obtained: Yield (%) | | | |
|---|---|---|---|---|
| | 1 | 2 | 3 | 7 |
| 1 | 84 | 1 | 1 | 2 |
| 2 | 77 | 2 | 1 | 3 |
| 5 | 74 | 5 | 3 | 6 |
| 10 | 74 | 6 | 7 | 7 |
| 15 | 74 | 5 | 9 | 7 |

When the oxidation is performed with hydrogen peroxide in a biphasic system, better diazepam conversion and yields in products are obtained with trifluorotoluene in the presence of hexafluoroisopropanol in place of the dichloromethane/acetonitrile solvent system.

Preliminary results from additional experiments currently underway confirm the efficacy of the process of the invention for the oxidation of compounds with relatively different structural parameters.

What is claimed is:

1. A process for obtaining potential metabolites of a drug, the process comprising:

reacting a drug with an oxidizing agent in a reaction medium comprising a metalloporphyrin and an inert aromatic solvent;

recovering reaction products; and identifying the reaction products;

wherein the metalloporphyrin is represented by formula 1,

1

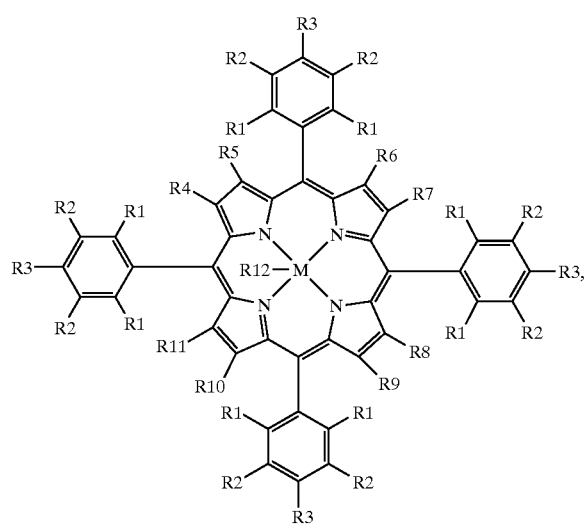

in which R1, R2, R3, R4, R5, R6, R7, R8, R9, R10, and R11 are independently hydrogen or an electron-withdrawing group;

R12 is Cl or acetate; and

M is iron, manganese, chromium, ruthenium, cobalt, copper or nickel.

2. The process of claim 1, wherein the inert aromatic solvent is a polyhalogenated aromatic solvent.

3. The process of claim 2, wherein the polyhalogenated aromatic solvent is trifluorotoluene.

4. The process of claim 1, wherein the reaction medium further comprises a co-solvent capable of increasing the solubility of the drug in the reaction medium.

5. The process of claim 4, wherein the co-solvent is a polar and poorly nucleophilic solvent.

6. The process of claim 4, wherein the co-solvent is 2,2,2-trifluoroethanol or 1,1,1,3,3,3-hexafluoro-propan-2-ol.

7. The process of claim 4, wherein the co-solvent concentration ranges between 1% and 30%.

8. The process of claim 1, wherein the reaction medium comprises a biphasic solution.

9. The process of claim 8, wherein the reaction medium comprises an inert aromatic solvent and a co-solvent, the co-solvent having the capability of transferring the drug between phases.

10. The process of claim 8, wherein the co-solvent is hexafluoroisopropanol.

11. The process of claim 8, wherein the reaction medium comprises a first aqueous phase that includes the oxidizing agent and a second organic phase that includes the drug, the metalloporphyrin, and the inert aromatic solvent.

12. The process of claim 11, wherein the second phase includes a co-solvent having the capability of transferring the oxidizing agent between phases.

13. The process of claim 12, wherein the co-solvent is water-miscible.

14. The process of claim 12, where the co-solvent is 1,1,1,3,3,3-hexafluoro-propan-2-ol.

15. The process of claim 9, further comprising introducing a phase-transfer catalyst into the reaction medium, the phase-transfer catalyst having the capability of allowing the transfer of reactants from between phases.

16. The process of claim 15, wherein the phase-transfer catalyst is a tetraalkyl ammonium salt.

17. The process of claim 16, wherein the tetraalkyl ammonium salt is dodecyl-trimethyl-ammonium bromide.

18. The process of claim 1, wherein R1, R2, and R3 of formula 1 are independently hydrogen, Cl, F, Br or $SO_3Na$.

19. The process of claim 1, wherein R4, R5, R6, R7, R8, R19, R10, and R11 of formula 1 are independently hydrogen, Cl, F, Br, $NO_2$, CN or $SO_3Na$.

* * * * *